(12) United States Patent
Jeong et al.

(10) Patent No.: US 7,763,159 B2
(45) Date of Patent: Jul. 27, 2010

(54) NANOCOMPOSITE SOLUTION WITH COMPLEX-FUNCTION AND METHOD FOR PREPARATION THEREOF

(75) Inventors: Chul-sang Jeong, Garak Town #206-1201, 1175, Hadan-dong, Saha-gu, 604-020 Pusan (KR); Moon-young Jeong, Gimhae-si (KR); Byoung-chan Kim, Gimhae-si (KR); Myung-soo Lee, Gimhae-si (KR)

(73) Assignee: Chul-Sang Jeong (KR)

( * ) Notice: Subject to any disclaimer, the term of this patent is extended or adjusted under 35 U.S.C. 154(b) by 1191 days.

(21) Appl. No.: 10/569,540

(22) PCT Filed: Dec. 26, 2003

(86) PCT No.: PCT/KR03/02855

§ 371 (c)(1),
(2), (4) Date: Feb. 23, 2006

(87) PCT Pub. No.: WO2005/019096

PCT Pub. Date: Mar. 3, 2005

(65) Prior Publication Data

US 2007/0009672 A1    Jan. 11, 2007

(30) Foreign Application Priority Data

Aug. 23, 2003    (KR) .................. 10-2003-0058489

(51) Int. Cl.
C25D 1/00    (2006.01)
C25D 3/46    (2006.01)
B82B 3/00    (2006.01)

(52) U.S. Cl. .................. 205/352; 205/144; 205/263

(58) Field of Classification Search .................. None
See application file for complete search history.

(56) References Cited

U.S. PATENT DOCUMENTS

| 2,892,797 | A | 6/1959 | Alexander et al. |
| 3,252,917 | A | 5/1966 | Mindick et al. ............. 252/313 |
| 6,214,299 | B1 | 4/2001 | Holladay et al. ....... 422/186.21 |
| 6,261,385 | B1 | 7/2001 | Nomura et al. ............. 148/301 |
| 6,277,169 | B1* | 8/2001 | Hampden-Smith et al. .... 75/336 |
| 6,287,639 | B1 | 9/2001 | Schmidt et al. ............. 427/387 |
| 2002/0121315 | A1 | 9/2002 | Nomura et al. ............. 148/302 |

FOREIGN PATENT DOCUMENTS

| CN | 1384150 | 12/2002 |
| CN | 1427041 A | 7/2003 |
| JP | 03-122162 A | 5/1991 |
| JP | 11-025759 A | 1/1999 |
| JP | 2002-019314 A | 1/2002 |
| JP | 2002-120467 A | 4/2002 |
| JP | 2002-179515 | 6/2002 |
| KR | 1998-0018045 | 6/1998 |
| KR | 1998-0066527 | 12/1998 |
| KR | 1999-0083918 | 12/1999 |
| KR | 1020000018196 A | 4/2000 |
| KR | 1020000021401 A | 4/2000 |
| KR | 1020010001169 A | 1/2001 |
| KR | 1020010070070 A | 7/2001 |
| KR | 1020010078858 A | 8/2001 |
| KR | 2003-0075229 | 9/2003 |

OTHER PUBLICATIONS

Z. Jiang et al, "Seed-Mediated Growth Technique for the Preparation of a Silver Nanoshell on a Silica Sphere", Oct. 2003, Journal of Physical Chemistry B, vol. 107, No. 45, pp. 12411-12415.*
T. Kim et al, "Silver-nanoparticle dispersion from the consolidation of Ag-attached silica colloid", May 2004, Journal of Material Res., vol. 19, No. 5, pp. 1400-1407.*
Kobayashi et al, "Deposition of Silver Nanoparticles on Silica Spheres by Pretreatment Steps in Electroless Plating", Apr. 2001, Chemical Materials, vol. 13, No. 5, pp. 1630-1633.*
Westcott et al, "Formation and Adsorption og Gold Nanoparticles onto Functionalized Silica Nanoparticle Surfaces", Aug. 1998, Langmuir, vol. 14, No. 19, pp. 5396-5401.*
International Search Report; PCT/KR2003/002855; Dated: May 21, 2004.
Li et al.; "Preparation of Ag/SiO2 Nanosize Composites by a Reverse Micelle and Sol-Gel Technique", American Chemical Society, 1999, vol. 15, No. 13, pp. 4328-4334.
Lawless et al.; "Reduction and Aggregation of Silver Ions at the Surface of Colloidal Silica"; American Chemical Society, 1994, vol. 98, No. 38, pp. 9619-9625.
Muniz-Miranda; "Silver-doped silica colloidal nanoparticles. Characterization and optical measurements"; Colloids and Surfaces A: Physicochem Eng. Aspects 217, 2003, pp. 185-189.
German Office Action for application No. 10394287.4-54 dated Oct. 19, 2009 with English translation.
Chinese Office Action mailed Jan. 9, 2009 for Publication No. 2003801104296; with English Translation.
Japanese Office Action mailed Mar. 4, 2009, citing Japanese reference Nos. 11-025759A, 03-122162A, 2002-019314A and 2002-120467A.
Korean Intellectual Property Office Notice of Official Action for Application No. 10-2003-0058489, Feb. 2006.

* cited by examiner

Primary Examiner—Harry D. Wilkins, III
(74) Attorney, Agent, or Firm—Cantor Colburn LLP

(57)    ABSTRACT

A method for preparation of nanocomposite solution, comprises preparing basic silica colloid aqueous solution; providing an electrolysis apparatus by installing a negative electrode containing aluminum and a positive electrode containing silver into the basic silica colloid aqueous solution; and forming nanocomposite by applying voltage to the respective electrodes of the electrolysis apparatus. With this configuration, the present invention provides a method of manufacturing solution dispersed with nanocomposite, further particularly to, a method of manufacturing nanocomposite solution having excellent storability and thermal stability and containing silver having antibacterial function, far infrared radiation function, deodorization function.

5 Claims, 7 Drawing Sheets

NANOCOMPOSITE SOLUTION WITH COMPLEX-FUNCTION AND METHOD FOR PREPARATION THEREOF

FIELD OF THE INVENTION

The present invention relates to a nanocomposite solution with multi-function and a method for preparation thereof.

BACKGROUND ART

The present invention relates to a nanocomposite solution with multi-function and a method for preparation thereof, further particularly to, solution in which nano-sized silica or silver dispersed in a combined state in water or organic solvent such as dimethylformamide (DMF), Dimethylacetamide (DMAC), etilenglicol (EG), glycerine and a method for preparation thereof.

A representative manufacturing process of silica colloid solution used in the present invention is disclosed in the U.S. Pat. Nos. 2,892,797 and 3,252,917. According to the disclosed manufacturing process, the silica colloid solution is manufactured in a method of controlling proper concentration by extracting silica of a controlled particle size as acid is added in water glass and by passing sodium and anion in the solution through anion exchange resin and ion exchange resin, respectively.

A process of manufacturing nano particles of high purity silver is divided into a top-down method of manufacturing the high purity silver of small size in a bulk state, and a bottom-up method of manufacturing by combining tens of silver atoms or silver ions. A particle of nano size always forms an oxidized film on a surface thereof when it is exposed on air because the atmosphere of the earth is mainly full of oxygen. Accordingly, the oxidized film always exists on the surface of a nano particle of pure metal. The oxidized film becomes relatively thicker in a nano state than in the bulk state, making metal particles of nano size less effective. Also, the particles of nano size hardly exist separated from each other because an agglomeration always occurs among the particles due to a tendency that each particle minimizes its surface area. However, in dispersion media such as water, or organic solvent, the particles of nano size can exist stably according to the kind of the dispersion media, and concentration and degree of agglomeration differ according to each particle. Particularly, the water is used as the dispersion media of the nano particle because the water is most common material on the earth, most environment-friendly, and applicable to broad application fields. Hereinbelow, conventional technologies related to manufacturing of silver particle solution of nano size are described.

A method of manufacturing and an application of silver sol with a silver particle having size between 1 and 100 nm dispersed in a medium with weight percentage ranging from 1 to 80 are disclosed in Korean patent publication no. 1998-018046. According to the disclosure, a silver corpuscle is manufactured by allowing silver composition solution to react with reducing agent under a temperature ranging from 5 to 50° C. and an agitation speed ranging from 1,000 to 10,000 rpm. The manufactured silver corpuscles are collected by a centrifugal separator, and dispersed in the medium again. The silver sol can be processed to be transparent conductive coating agent by adding bonding agent as necessary and can be applied to a cathode ray tube.

A method of manufacturing composite metal particle of nano size in solution using surface active agent is disclosed in Korean patent publication no. 2000-0018196. According to this disclosure, composite metal ion solution dissolved with two kinds or more of salt composites such as gold, silver, iron, platinum, and zinc is added with one kind or more of reducing agents such as hydrazine, $NaBH_4$, $LiAlBH_4$, and oxo compound to be resolved into composite metal particles. In this process, the surface active agents such as hydrocarbon type, silicon type, and fluorocarbon type is added to block growing of the composite metal particles and to keep the size of the particle at nano size. Also, antioxidant such as butylhydroxy toluene, and vitamin E derivative is used to prevent oxidization of a surface of metal particles. The manufactured composite metal particles are used for the purposes of antibacterial, sterilization, medicine, abrasive material, antistatic, electromagnetic wave protection, photosensitivity.

A method of manufacturing colloid of nano size using radiation exposure is disclosed in Korean patent publication no. 2001-0078858. Specifically, in-process material is removed by adding alcohol after silver salt such as $AgNO_3$, $AgClO_4$, and $AgClO_3$ is melt in water. After a nitrogen substitution by adding colloid stabilizer, silver colloid particles having constant distribution is manufactured by radiation exposure. Herein, the alcohol is chosen from a group of methanol, ethanol, isopropanol, normal propanol, and butanol, and the stabilizer is chosen from a group of sodium dodecyl sulfate, polyvinyl alcohol, and polyvinylpyrollidone. The colloid manufactured according to the method disclosed in the above invention can be used as scattering enhancer for raman spectrograph, addition agent of ink activator, antibacterial and antibiosis material, conductive adhesive, and electromagnetic wave blocker.

A method of manufacturing antibacterial soup containing silver of high density using silver colloid is disclosed in Korean patent publication no 2001-0069644. In other words, it discloses a method of manufacturing low-cost antibacterial silver soup that overcomes disadvantages of a conventional silver soup such as high cost, and limited mass production. The silver colloid used therein contains the silver having high density of over 50,000 ppm and manufactured in a state of silver salt solution using reducer and surface active agent. Accordingly, this disclosure made profitable mass production possible in manufacturing the soup.

A manufacturing apparatus of gold and silver colloid is disclosed in Korean Utility Model first publication No. 2000-0021401. In installing the manufacturing apparatus of the gold and silver colloid comprising a power supply, a timer, an electrolysis circuit line, and silver plate, parts on the silver plates with small area are installed to be opposed with a constant distance. Meanwhile, a standardized product used for containing distilled water, or purified water is employed as a container.

A manufacturing apparatus of silver solution being capable of manufacturing the silver solution efficiently in a rapid speed is disclosed in Korean Utility Model first publication No. 2001-0001169. The manufacturing apparatus comprises a body comprising an inner drum forming space where distilled water is accommodated inside, an outer drum surrounding a circumference of the inner drum and accommodating the inner drum, and a cover opening/closing an upper opening of the body; two silver electrode rods inserted into the distilled water in the body; a power supply applying an alternative voltage of 110 V or 220 V with frequency of 60 Hz to the silver electrode rods; a frequency modifier to increase the frequency; and a transformer to increase voltage. Also, this apparatus is distinctive in that it can manufacture the silver solution in a short time.

A method of manufacturing metal colloid, particularly platinum colloid is disclosed in Korean Utility Model first publication No 2001-0070070. According to this disclosure, A temperature during a reducing process can be controlled by adding metal ion solution and ph compensation agent into solution mixed with water and the surface active agent. The platinum colloid can be manufactured by reducing metal ion by controlling the temperature in a manner described above and stirring. Herein, ethanol is used as the reducer, and polysorbate 80 is used as the surface active agent, and sodium carbon hydrogen is used as the pH compensation agent. An oxidization reduction potential after completion of the reduction process is over −400 mV.

A method of electrically manufacturing colloid having particle size of 30 nm or below with one or more of a group comprising metals from group Ib, group IIb, group III, group IV, group V, group VI, group VIIb, group VIII, lanthanoid, actinoid is disclosed in U.S. Pat. No. 5,925,463. According to this disclosure, after metal electrodes are dipped in electrolytic cell added with electrolyte, a reduction process occurs on a negative electrode with currents applied. Herein, Quaternary amine composite such as Tetraoctylammonium bromide is added as stabilizer, and organic solvent such as tetrahydro furan is used as dispersion media.

A manufacturing apparatus of silver colloid and a method of manufacturing the silver colloid are disclosed in U.S. Pat. No. 6,214,299. The manufacturing apparatus comprises plurality of electrodes attached with silver wire and installed on a 15-gallon container in each direction centering a rotating stirring rod. Herein, each electrode is connected to a transformer. By filling the container with water and supplying the electrode with power, silver particles are separated from the silver wire and dissolute. In this way, the silver colloid is manufactured.

High purity silver can exist as an ion or a particle in water dispersion media with extremely low concentration. Also, it can exist in several ppm, which is a relatively high concentration, with a form of complex compound (ion composition) with another anion. The High purity silver of such state is called colloidal silver.

One method of dispersing silver nano particles stably in high concentration in water dispersion media or organic solvent dispersion media is preventing the silver from settling according to Stokes' Law by adjusting viscosity of the water dispersion media or the organic dispersion media in a state of nano particle (viscosity adjuster is added).

Also, by applying ionic media such as the surface active agent on a surface of nano silver particles, particles can be ionized with a same sign so that the nano silver particles are dispersed stably by retraction force applied by ionic character among particle of same ionic sign. Another method is combining with stable composition having ionic character in a form of complex ionization or complex compound in the water dispersion media or the organic solvent dispersion media.

However, nano silver solution having the nano silver particles dispersed in the water dispersion media or the organic solvent dispersion media dose not contains nano particles in a complete metal state, but contains ionic character partially. Accordingly, as time passes by, the ionic character or the complex ionization composition becomes unstable, causing deposition or settling in the container. Also, as the nano silver solution being unstable thermally and dispersed in the water dispersion media or the organic solvent dispersion media is heated, agents such as adjuster, stabilizer, surface active agent, complex ionization composition lose their function. Accordingly, agglomeration occurs among most of the particles, and the nano silver particles are settled. Most of the conventional silver nano colloidal products are restricted in industries due to the ionic character, instability in high temperature.

DISCLOSURE OF INVENTION

Accordingly, it is an aspect of the present invention to provide a method of manufacturing solution dispersed with nanocomposite, further particularly to, a method of manufacturing nanocomposite solution having excellent storability and thermal stability and containing silver having antibacterial function, far infrared radiation function, deodorization function.

Additional aspects and advantages of the invention will be set forth in part in the description which follows and, in part, will be obvious from the description, or may be learned by practice of the invention.

The foregoing and other aspects of the present invention are achieved by providing a method for preparation of nanocomposite solution, comprising: preparing basic silica colloid aqueous solution; providing an electrolysis apparatus by installing a negative electrode containing aluminum and a positive electrode containing silver into the basic silica colloid aqueous solution; and forming nanocomposite by applying voltage to the respective electrodes of the electrolysis apparatus.

According to an aspect of the invention, temperature when applying the voltage is between 30 and 100° C.

According to an aspect of the invention, content of silica in the basic silica colloid aqueous solution is between 0.1 and 30 weight percentage.

According to an aspect of the invention, PH of the basic silica colloid aqueous solution is between 8 and 12 PH.

According to an aspect of the invention, the method for preparation of the nanocomposite solution further comprises applying organic solvent to the nanocomposite solution and removing water.

According to another aspect of the present invention, the above and other aspects may be also achieved by providing Nanocomposite solution manufactured according to the method for preparation of the nanocomposite solution.

According to another aspect of the present invention, the above and other aspects may be also achieved by providing Nanocomposite solution comprising nanocomposite and dispersion media comprising silver particles with size between 1 and 10 nm and silica particles having size between 3 and 50 nm.

According to an aspect of the invention, the nanocomposite further comprises aluminum.

According to an aspect of the invention, the silver particle and the silica particle are bound to each other.

According to another aspect of the present invention, the above and other aspects may be also achieved by providing nanocomposite comprising silver particles having size between 1 and 10 nm and silica particles having size between 3 and 50 nm.

According to an aspect of the invention, the silver particle and the silica particle are bound to each other.

According to an aspect of the invention, the nanocomposite according to claim further comprises aluminum.

BRIEF DESCRIPTION OF DRAWINGS

The above and/or other aspects and advantages of the present invention will become apparent and more readily appreciated from the following description of the embodiments, taken in conjunction with the accompany drawings of which.

MODES FOR CARRYING OUT THE INVENTION

Figure 1:
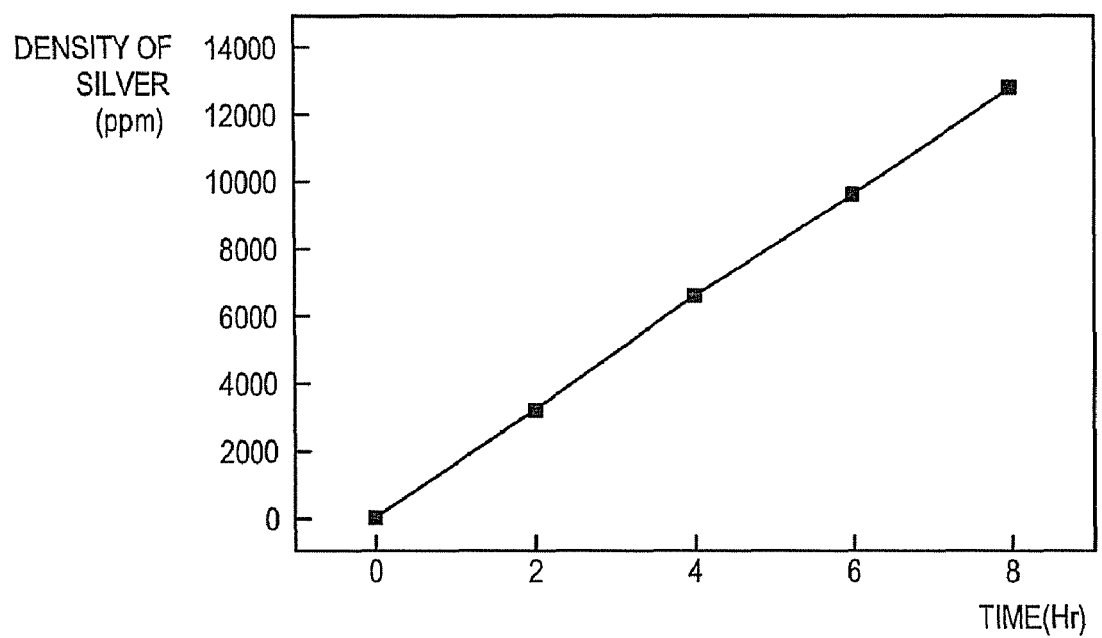
FIG. 1 is a graph representing variation of content of silver according to manufacturing duration of an embodiment of the present invention.

Reference will now be made in detail to the embodiments of the present invention, examples of which are illustrated in the accompanying drawings, wherein like reference numerals refer to like elements throughout. The embodiments are described below in order to explain the present invention by referring to the figures.

An embodiment of the present invention employed an unique electrolysis method to manufacture nanocomposite solution. This electrolysis method distinctively uses basic silica colloid aqueous solution as electrolysis solution. Content of the silica particle in the basic silica colloid aqueous solution is preferably between 0.1 and 30 weight percent. However, dispersion agent (surface active agent) is required because stable nanocomposite cannot be formed when the content is below 0.1 weight percent and agglomeration occurs among the silica particles when the content is over 30 weight percent. The silica colloid solution should be electropositive because the silver has a tendency to stay in an ion state with positive electric charges in acid solution, and silver ion cannot be combined on a surface of the silica but reduced on a negative electrode in such tendency. A pH of the basic silica colloid solution is preferably between 8 and 12. The silica colloid becomes unstable when pH is below 8 which is neutral zone, and the silica particles are separated into silicate ions when pH is over 12. A reaction temperature is preferably between 30° C. and 100° C. A velocity of the electrolysis decreases with requiring more expense when the reaction temperature is below 30° C. while compressing apparatus is required when the reaction temperature exceeds 100° C.

An electrolysis apparatus comprises two electrodes shaped like plates in a same way a conventional method employs. Herein, the electrodes may be provided in a cylindrical shape to maximize an area of a positive electrode so that the amount of the silver ions detached from the positive electrode can be maximized. Meanwhile, it is preferable to apply ultrasound wave on the positive electrode or to rotate the positive electrode to minimize the content of the silica, aluminum, and the silver deposited on the positive electrode. Herein, the negative electrode may be provided in a shape of a rod or a cylinder. A duration of the electrolysis may vary depending on a target content of the aluminum and the silver. The duration of the electrolysis in the present invention may vary from 5 minutes to 12 hours.

In the conventional method in which the silica colloid aqueous solution is used as the electrolysis solution, if the basic silica colloid is anion, the silica particles are deposited on the positive electrode in the electrolysis solution in a short time, regardless of the kind of metals used for the positive and negative electrodes. However, as the positive electrode is coated with the silica particles across the whole area of the positive electrode, the electrolysis reaction on the positive electrode is terminated, which makes the electrolysis on both the positive and negative electrodes stop.

For above reasons, the nanocomposite has extremely small content of the silver and its applicability is somewhat limited. To solve such problems, the present invention employs the basic silica colloid aqueous solution as the electrolysis solution. An electrode made of alloy containing pure aluminum or aluminum is installed as the negative electrode to make the aluminum dissolve as it dissolves in usual basic solution regardless of the electrolysis. Also, a temperature is increased to increase the reaction velocity. An amount of the deposition of the silica on the positive electrode conspicuously decreases according to this method, which makes reactions on the positive and negative electrodes keep going. It is presumed that a dissolution reaction of the aluminum and a hydrogen generating reaction on a surface of the aluminum contribute to such results altogether.

In a process of manufacturing the nanocomposite solution according to the present invention, the silver is dissipated into the electrolysis solution by ionization on the positive electrode in the basic silica colloid electrolysis solution. On the negative electrode, the hydrogen generating reaction occurs efficiently, and the dissolution reaction caused by the basic silica colloid occurs on the negative electrode concurrently, regardless of the electrolysis reaction. Accordingly, as the silica particle and the silver particle are combined into one particle of an in-situ, and the nanocomposite of the present invention is formed. In this process, when forming the nanocomposite, the aluminum is presumed to exist in a form of solid solution or an amorphous aluminum particle of nano size within a nano silver crystal. It is presumed that a formation of such nanocomposite is made by the electrolysis, and a complex reaction of ionization energy caused by the dissolution reaction of the aluminum regardless of the electrolysis. Such presumption is derived from that the silica, the silver, and the aluminum are not combined but exist as separate ions when colloidal silica, silver nitrate solution, and sulfate aluminum solution are mixed.

As the process goes, the silver particle in the nanocomposite solution turns from yellow, or color of nano silver in the solution, gradually into black through red. Also, a concentration of hydrogen ion, or pH, varies from basic to neutral. When a reaction is completed with a wanted content, the nanocomposite solution turns into opaque black solution, and this solution turns into transparent yellow solution if the solution is diluted to have concentration of 1 ppm again. Accordingly, it is noted that, the color of the solution turns from yellow into black not only as the concentration of the nanocomposite increases, but also as the concentration of the silver contained in the nanocomposite varies. With a result of analysis on the nanocomposite dried to be in a solid state, it is found that particles comprising the silica, and the silver have an average size ranging from 10 to 20 nano size. The size depends on a size of the silica particle, and it is tolerable even if the size of the silica particle is little smaller or bigger than the average size. As an example, an average size between 3 nm and 50 nm will be tolerable. With a result from an analysis on a crystal structure by an X-ray diffraction apparatus, the silica is identified in dried powder, but existence of the aluminum was not clear. However, the aluminum is presumed to exist in a state of solid solution on the silver crystal or in an amorphous form. A minute structure of the three components can be identified by a transmission electron microscope (TEM), and a size of the nano particle is between 1 and 3 nm. The size depends on the size of the silica and it can be as big as up to 10 nm. An analysis on those data is represented in a result of an analysis on example tests. Also, original solution, 100-times diluted solution, and 1000-times diluted solution of the nanocomposite manufactured according to the present invention has colors of black, red, and yellow, respectively. Herein, the content of the nanocomposite is proximately 10 weight percent, and the color of the nanocomposite may vary according to the content of the nanocomposite.

When manufacturing the nanocomposite having functions such as antibacterial according to the process described above, the problem that a storage duration decreases due to the ionic character can be solved, and the nanocomposite becomes so thermally stable that it can exist stably even if the nanocomposite is heated up to 100° C. Also, it solves a problem of noxiousness caused by the stablizer, the viscosity adjuster, and the surface active agent of the nano colloidal solution. Applicability of the solution is very broad because an unnecessary anion does not exist as a contaminant. A method of the nanocomposite solution according to the present invention is not limited to manufacturing conditions above.

Hereinbelow, example tests are described to represent results of measuring structural characteristics and physical properties of particles in the nanocomposite solution. Embodiments are examples applying compositions of the present invention to various materials.

The present invention will be specified further with preferred embodiments and example tests described below. However, the present invention is not limited by the preferred embodiments and the example tests described below.

A First Embodiment

An 18-liter container is filled with the basic silica colloid aqueous solution having pH of 11. An electrode made of the silver having the purity of 99.99 weight percent is used as a positive electrode while an electrode made of the aluminum having the purity of 99.8 weight percent is used as a negative electrode. Area for each electrode is provided to be proximately 660 cm². Herein, the reaction temperature is kept at 90° C. to increase the reaction velocity and is controlled by an automatic temperature controller. Variation of level of electrolysis solution caused by evaporation is controlled by adding proper amount of pure water. Herein, voltage applied to the positive and negative electrodes is 120 V, and current thereof is 3 ampere. As the electrolysis proceeds, the nanocomposite is formed as the silica, the silver are combined as the in-situ in the solution by the electrolysis reaction. Variation of the content of the silver in the solution according to passage of reaction time is shown in FIG. 1, and composition after reaction for 8 hours is shown in Table 1.

Example Test 1

The content of components of the composition is analyzed with an inductively coupled plasma atom emission spectroscope. Results are shown in Table. 1.

TABLE 1

| components | content (ppm) |
|---|---|
| Ag | 10605.0 |
| Al | 1896.0 |
| Na | 1278.4 |
| Si | 31720.0 |

Example Test 2

Figure 2:
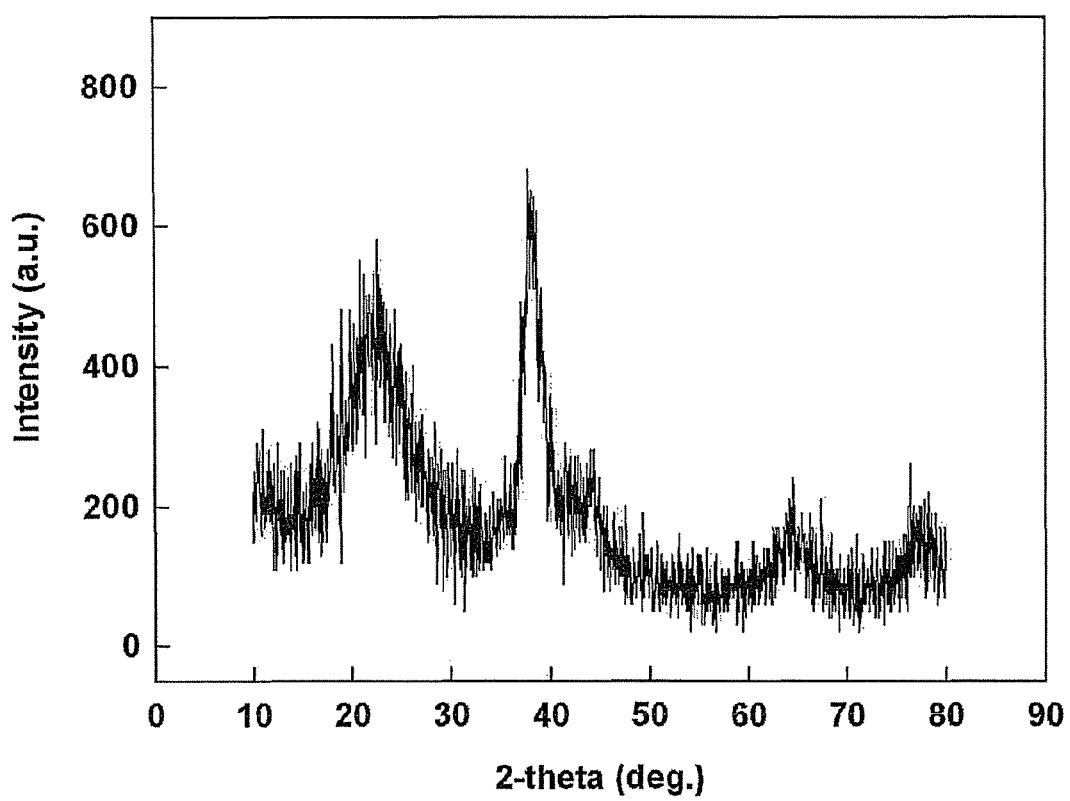
FIG. 2 is a graph representing an X-ray diffraction pattern of nanocomposite according to the embodiment of the present invention.

An X-ray diffraction analysis was implemented to observe a structure of the nanocomposite. A sample was smashed after dried under 80° C. for 24 hours before the analysis. FIG. 2 illustrates a result of the analysis. A wide band of peaks about 20 indicates absorption peaks of the silica, while peaks about 40, 65, 80 are absorption peaks of the silver.

Example Test 3

Figure 3:
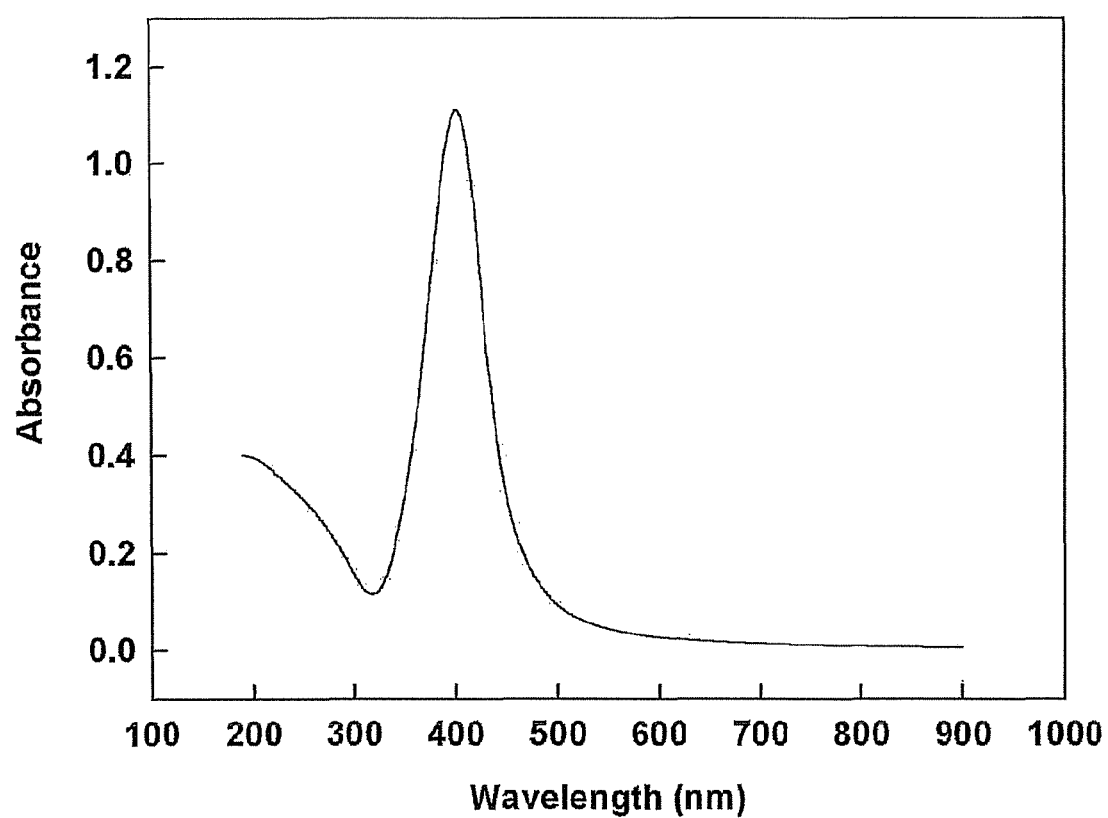
FIG. 3 is a graph representing an ultraviolet-visible ray absorption spectrum of nanocomposite solution.

An ultraviolet-visible ray absorption spectrum was measured to observe optical property of the nanocomposite. FIG. 3 illustrates a result thereof. According to the drawing, an absorption peak appears between 380 nm and 400 nm.

Example Test 4

Figure 4:
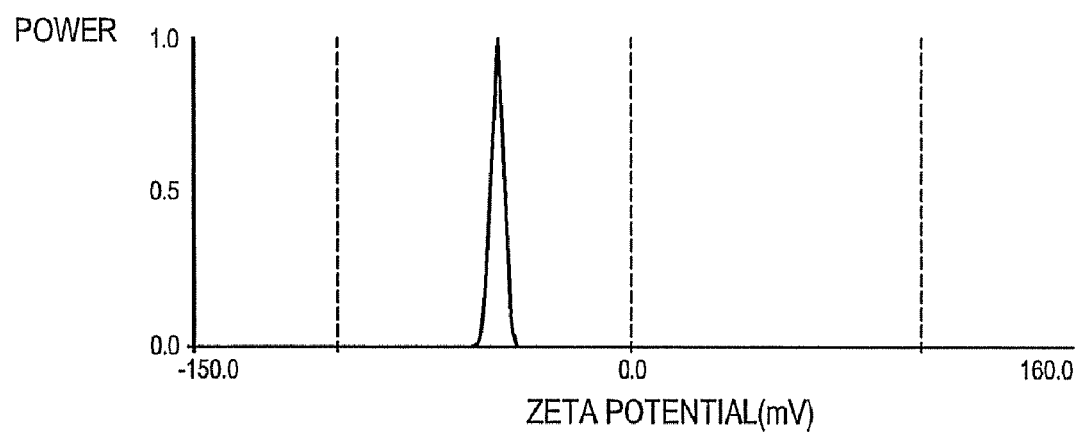
FIG. 4 is a distribution graph of surface charges of particles in the nanocomposite solution.

A zeta potential analysis was implemented to measure a surface charge of particles in the nanocomposite solution. A result shows an average charge has a stable particle retractive force of −41.31 mV. A distribution pattern is shown in FIG. 4.

Example Test 5

Figure 5:
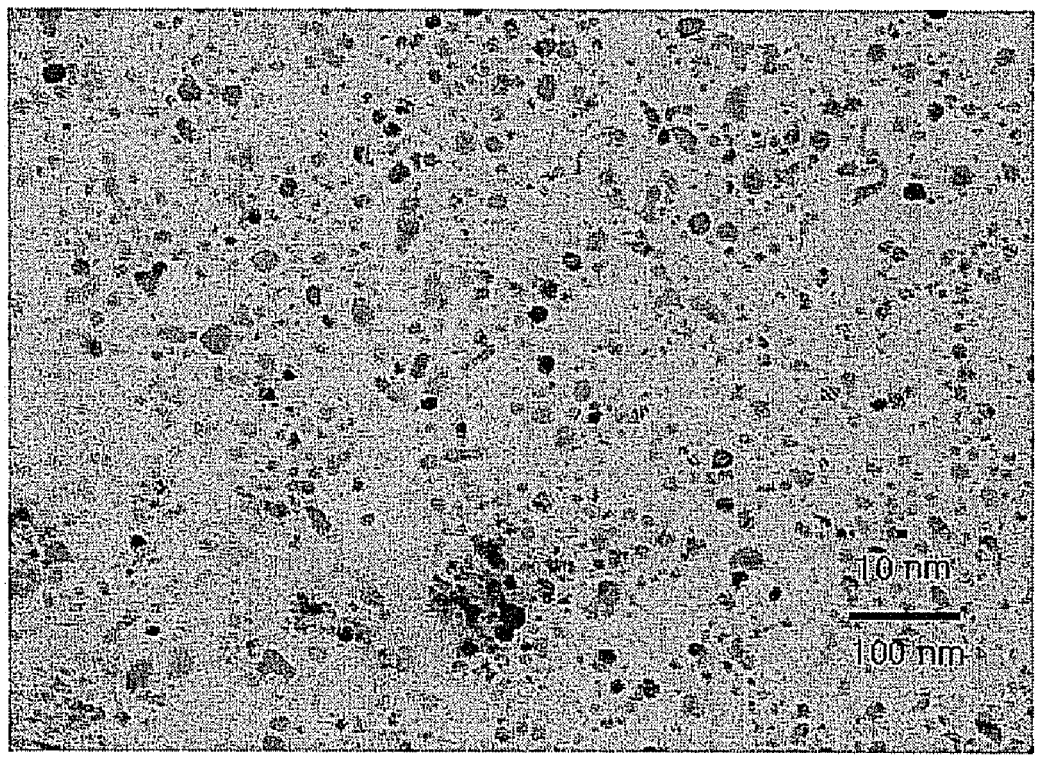
FIG. 5 is a photograph 1 of a transmission electron microscope (TEM) on the nanocomposite.
Figure 6:
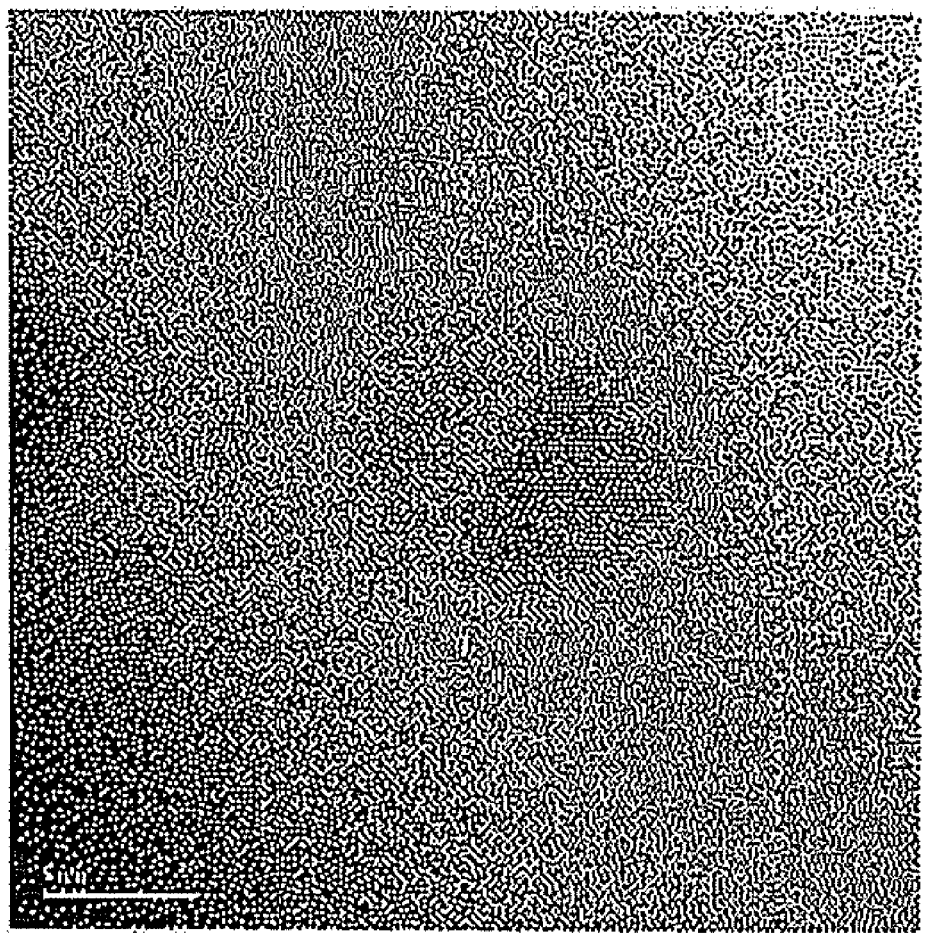
FIG. 6 is a photograph 2 of TEM representing silver particles in the nanocomposite.

A minute structure of the particles in the nanocomposite solution was observed with TEM. FIGS. 5 and 6 show results. FIG. 5 shows the distribution and size of the particle, and FIG. 6 shows a single structure of the particle. In FIG. 6, black circles are the silver, and areas other than the black circles are the silica.

Hereinbelow, applications of the nanocomposite manufactured according to the embodiment of the present invention to various fields will be described. However, the fields of the application is not limited only to the fields described below. The nanocomposite refers to a particle that the silica and the silver are combined in the nanocomposite solution. In the embodiments described below, the nanocomposite solution described in an embodiment 1 is used in other embodiments unless specified otherwise. However, following nanocomposite solution can be employed to show compatible effect.

The silver in the nanocomposite is distributed with a size between 1 nm and 10 nm, and may exist by combining with the silica having a size between 3 nm and 50 nm. Also, a weight ratio of the silver and the silica may be between 1:1 and 1:15. Also, the nanocomposite may further comprise the aluminum. In such case, a weight ratio of the aluminum and the silver may be between 1:1 and 1:10. The aluminum may exist by combining with the silver and the silica. The content of the silver in the nanocomposite solution may be between 0.01 and 5 weight percent. Although the embodiments mainly use the aqueous solution of the nanocomposite, the water may be used by substitution into the organic solvent as necessary. The substitution may employ a method of evaporating the water after adding the organic solvent to the nanocomposite solution, or a method of making a vacuum state with heating.

A Second Embodiment

Because the nanocomposite solution according to the present invention, has functions such as antibacterial, deodorization, anti-fungal, far infrared radiation, it may be used directly with a spray. Results from various function test implemented on the nanocomposite solution are shown in FIG. 2.

The antibacterial test was implemented on two bacteria according to a shake-flask method (FC-TM-19)-2001 of FITI testing & research institute of Korea. After a testing bacterial solution containing 1.0 weight percent of the nanocomposite solution is cultivated at 35° C. for 10 minutes, the number of the bacteria was counted.

TABLE 2

| testing bacteria | item | Blank | Sample |
|---|---|---|---|
| *Staphylococcus aureus* (ATCC 6538 P) | initial number of bacteria (number/ml) | $1.6 \times 10^5$ | $1.6 \times 10^5$ |
| | number of bacteria after 10 minutes (number/ml) | $1.7 \times 10^5$ | <10 |
| | decreasing rate (%) | | >99.9 |
| *E coli* (ATCC 8739) | initial number of bacteria (number/ml) | $1.4 \times 10^5$ | $1.4 \times 10^5$ |
| | number of bacteria after 10 minutes (number/ml) | $1.6 \times 10^5$ | <10 |
| | decreasing rate (%) | | >99.9 |

A degree of deodorization is measured by a gas detecting tube method on ammonia gas with 2 g of the powered nanocomposite acquired by smashing after being dried at 80° C. for 24 hours. A result is shown in Table. 3.

TABLE 3

| | | measuring time (minute) | | | |
|---|---|---|---|---|---|
| | | 5 | 15 | 30 | 60 |
| gas concentration (ppm) | blank | 250 | 220 | 195 | 180 |
| | sample | 10 | 5 | <5 | <5 |
| deodorization rate (%) | | 96.0 | 97.7 | >97.7 | >97.7 |

A testing on an anti-fungal degree is implemented on a sample that was acquired by drying the solution filtered through a standard filter paper with a composition bacteria of *aspergillus niger* (ATCC 9642), *chaetomium globosum* (ATCC 6205), *penicillum pinophilum* (ATCC 11797), *gliocladium virens* (ATCC 9645), *aureobasidium pullulans* (ATCC 15233). As a result, the anti-fungal degree is determined to be class 0. A classification on the anti-fungal degree is as follows.

class 0—no fungi grown
class 1—fungi grown on less than 10% of a test piece
class 2—fungi grown on 10-30% of the test piece
class 3—fungi grown on 30-60% of the test piece
class 4—fungi grown on over 60% of the test piece To measure a radiation rate of the far infrared radiation and radiation energy, the solution was dried at 80° C. for 24 hours and smashed to be power. 3 g of the power was placed in a square shape for a test. The test was implemented by a black body comparison method with a wavelength ranging from 5 to 20 μm at 50° C., using a Fourier transform infrared spectroscope. As a result, the radiation rate of the far infrared radiation was measured to be 0.916, while the radiation energy was measured to be 425 W/m².

A Third Embodiment

The nanocomposite solution according to the embodiment of the present invention is effective in eradicating algae. Particularly, as it is highly effective in eradicating red algae, it can be used as material to prevent the red algae. To prove such effect, a test on preventing the red algae was implemented. An objective red algae is cochlodinium polykrikoides, and a density of the red algae is 2000 cells/ml. An eradication rate of the red algae is measured by taking a measurement from samples with various concentrations of the silver. A result from this test is shown in FIG. 4. This is on a level same with or higher than loess of highest class.

TABLE 4

| sample concentration | time | | | |
|---|---|---|---|---|
| | immediately | past 10 min | past 30 min | past 60 min |
| 0.01 ppm | 60~62% | 62~65% | 75~77% | 77~80% |
| 0.05 ppm | 68~70% | 70~74% | 75~77% | 80~82% |
| 0.1 ppm | 65~67% | 66~68% | 80~82% | 85~89% |
| 1.0 ppm | 80~82% | 90~93% | 95~96% | 96~98% |

A Fourth Embodiment

As the nanocomposite solution according to the embodiment of the present invention has functions of anti-fungal and anti-algae, it can be used as anti-fungal agent and an anti-algae agent for treating industrial cooling water. While applying, it can be used with liquidating the solution. Table. 5 represents a result on the number of remaining bacteria measured according to passage of time by adding the nanocomposite solution into the cooling water so that the concentration of the silver in the cooling water can be 1 ppm. It appears that the number of the remaining bacteria dwindles according to the passage of time. A same effect can be expected in the concentration of the silver of over 0.1 ppm.

TABLE 5

| | time | | | |
|---|---|---|---|---|
| | day 1 | day 2 | day 3 | day 4 |
| the number of bacteria | $5.0 \times 10^2$ | $2.0 \times 10^2$ | $5.0 \times 10^2$ | $1.6 \times 10^2$ |

A Fifth Embodiment

A heavy mesh merry fabric with functions of anti-fungal, far infrared radiation, and anti-static has been made by treating a heavy mesh merry fabric with the nanocomposite solution according to the embodiment of the present invention. A process of treatment employed a fabric padding method. The fabric was dipped in a dipping liquid containing the nanocomposite solution in a continuous process. After removing leftover moisture, the fabric was dried and crosslinkaged at a temperature between 150 and 180° C. Herein, the dipping liquid contains binder, softening agent, and crosslinkage agent.

An anti-fungal test on the heavy mesh fabric manufactured as described above was implemented according to a standard of KS K 0693-2001, and its results are as shown in Table. 6.

TABLE 6

| testing bacteria | items | Blank | Sample |
|---|---|---|---|
| Staphylococcus aureus | the initial # of bacteria (#/ml) | $1.4 \times 10^5$ | $1.4 \times 10^5$ |
| | the # of bacteria after 24 hrs (#/ml) | $6.3 \times 10^5$ | <10 |
| | decreasing rate (%) | | >99.9 |
| clepsiera neumonia | the initial # of bacteria (#/ml) | $1.5 \times 10^5$ | $1.5 \times 10^5$ |
| | the # of bacteria after 24 hrs (#/ml) | $6.3 \times 10^5$ | <10 |
| | decreasing rate (%) | | >99.9 |

A test was implemented to measure the far infrared radiation rate and the radiation energy on the fabric. This test is implemented with a sample of the heavy mesh merry fabric having size of 30×30 mm under the condition of wavelength between 5~20 μm and temperature 40° C. Also, a radiation rate of the sample against the black body is measured using a fourier conversion infrared prism. As a result, the far infrared radiation rate was taken to be 0.897, and the radiation energy to be 361.32 W/m².

A measurement test on a friction against voltage was implemented to find out about characteristics on chargeability of static charge. This test was implemented according to a method-8 described in KS K 0555-1983, with a condition of temperature 20+2° C. or 20−2° C., moisture 40+2% or 40−2% RH, and friction rotation speed 400 rpm, using a criterion cotton fabric. With such condition, the fabric treated with nanocomposite solution and the untreated fabric was charged respectively with the cotton fabric and the voltages were measured. As a result, the fabric treated with the nanocomposite solution is measured to have voltage below 10 V, while the untreated fabric is 2230 V.

A Sixth Embodiment

A non-woven fabric having functions of anti-fungal, far infrared radiation, anti-static is manufactured using a non-woven fabric such as polyester, polypropylene using the nanocomposite solution. A treatment process is a fabric padding method. The non-woven fabric is dipped in the dipping liquid containing the nanocomposite solution. After removing the leftover moisture, the fabric was dried and crosslinkaged at a temperature between 150 and 180° C. Herein, the dipping liquid may be the nanocomposite solution itself, or a liquidated nonocomposite solution. Also, it may contain the binder, that is most common acrylic, with weight percentage between 1 and 10.

The test on the anti-fungal on the non-woven fabric manufactured as described above is implemented according to the standard of KS K 0693-2001, and a result is shown in Table. 7.

TABLE 7

| testing bacteria | items | Blank | Sample |
|---|---|---|---|
| Staphylococcus aureus | the initial # of bacteria (#/ml) | $1.3 \times 10^5$ | $1.4 \times 10^5$ |
| | the # of bacteria after 24 hrs (#/ml) | $5.7 \times 10^5$ | <10 |
| | decreasing rate (%) | | >99.9 |
| clepsiera | the initial # of | $1.4 \times 10^5$ | $1.4 \times 10^5$ |

TABLE 7-continued

| testing bacteria | items | Blank | Sample |
|---|---|---|---|
| neumonia | bacteria (#/ml) the # of bacteria after 24 hrs (#/ml) | $6.6 \times 10^5$ | <10 |
| | decreasing rate (%) | | >99.9 |

A test on the deodoration was implemented with a gas detection method. A variation of the ammonia gas concentration was measured with a non-woven fabric sample according to passage of time and its result is shown in Table. 8. A rate on deodoration is represented by a equation of (gas concentration of Blank−gas concentration of the sample)/(gas concentration of Blank)×100.

TABLE 8

| | | measurement time | | | |
|---|---|---|---|---|---|
| | | 5 | 15 | 30 | 60 |
| gas concentration | Blank | 380 | 330 | 280 | 230 |
| | Sample | 220 | 175 | 140 | 105 |
| deodoration rate (%) | | 42.1 | 47.0 | 50.0 | 54.3 |

A test was implemented on the non-woven fabric to measure the far infrared radiation rate and the radiation energy. The test was implemented on a condition of wavelength between 5~20 μm and a temperature of 30° C. with a sample with size of 30×30 mm. Also, a radiation rate against the black body is measured using the fourier conversion infrared prism. As a result, the far infrared radiation rate is measured to be 0.823, while the radiation energy is 286.07 W/m².

To measure a chargeability of static electron against the non-woven fabric, a test on the friction against the voltage is implemented. This test is implemented according to a method-8 of KS K 0555-1983, with a condition of temperature 20+2° C. or 20−2° C., a moisture of 40+2% or 40−2% RH, and a friction rotation speed 400 rpm, using the criterion non-woven fabric. With such condition, the non-woven fabric treated with the nanocomposite solution and the untreated non-woven fabric are charged, respectively, and the voltages are measured. As a result, the non-woven fabric treated with the nanocomposite solution is measured to be 340 V, while the untreated non-woven fabric is 720 V.

A Seventh Embodiment

During manufacturing polyurethane foam in the present invention, the polyurethane foam having a function of anti-fungal, deodoration, far infrared radiation is manufactured by adding the nanocomposite solution into polyol and by foaming in a step that isocyanate and polyol are mixed. The added amount of the nanocomposite solution is preferably between 1 and 5 weight percentage on whole solution of the isocyanate and the polyol.

A test of anti-fungal on this polyurethane foam is implemented according to a shake-plask method (FC-TM-19)-2001. Sample fungus liquid containing 0.4 g of the polyurethane foam containing the nanocomposite solution is boiled for 24 hours at 35° C., and the number of the incubated bacteria was measured. The result is as shown in Table. 9.

TABLE 9

| testing bacteria | items | Blank | Sample |
|---|---|---|---|
| Staphylococcus aureus | initial number of bacteria (number/ml) | $1.6 \times 10^5$ | $1.6 \times 10^5$ |
| | number of bacteria after 24 hrs (number/ml) | $7.2 \times 10^5$ | <10 |
| | decreasing rate (%) | | >99.9 |
| E coli | initial number of bacteria (number/ml) | $1.5 \times 10^5$ | $1.5 \times 10^5$ |
| | number of bacteria after 24 hrs (number/ml) | $7.2 \times 10^5$ | <10 |
| | decreasing rate (%) | | >99.9 |

A test on deodoration of the polyurethane foam is measured according to the gas detection method. A variation of ammonia gas concentration is measured according to passage of time on 3.7 g of the sample. The result is as shown in Table. 10.

TABLE 10

| | | measured time (min) | | | | |
|---|---|---|---|---|---|---|
| | | 30 | 60 | 120 | 180 | 240 |
| gas concentration | Blank | 245 | 180 | 120 | 120 | 110 |
| | sample | 25 | 5 | <5 | <5 | <5 |
| deodoration rate (%) | | 89.8 | 97.2 | >97.7 | >97.2 | >97.2 |

A test measuring the far infrared radiation rate and the radiation energy is implemented on the polyurethane foam treated with the nanocomposite solution and the untreated polyurethane foam. The test was implemented on a condition of wavelength between 5~20 μm and a temperature of 30° C. with a sample with size of 30×30 mm. Also, a radiation rate against the black body is measured using the fourier conversion infrared prism. As a result, the far infrared radiation rate for the treated foam is measured to be 0.885, while the radiation energy is 356.417 W/m². Meanwhile, the far infrared radiation rate for the untreated foam is measured to be 0.868, while the radiation energy is 349.639 W/m².

An Eighth Embodiment

An adhesive with anti-fungal function is manufacture by adding the nanocomposite solution to an adhesive in this embodiment of the present invention. Among these, aqueous adhesive is added with the nanocomposite solution having 1 weight percentage concentration. However, the concentration may be between 0.1 and 5 weight percentage. For oil adhesive, the dispersion media is displaced with oil solvent such as dimethylformamide and Dimethylacetamide using an assortment distillation method before manufacturing. Same conditions are applied.

After manufacturing a sample as a film for the oil adhesive manufactured as described above, a test on an anti-fungal is implemented using a film contacting method (FC-TM-21)-2001. A result is as shown in Table. 11.

TABLE 11

| testing bacteria | items | Blank | Sample |
|---|---|---|---|
| Staphylococcus aureus | initial number of bacteria (number/ml) | $1.3 \times 10^5$ | $1.3 \times 10^5$ |
| | number of bacteria after 24 hrs (number/ml) | $6.4 \times 10^5$ | $1.3 \times 10^4$ |
| | decreasing rate (%) | | 99.8 |

TABLE 11-continued

| testing bacteria | items | Blank | Sample |
|---|---|---|---|
| E coli | initial number of bacteria (number/ml) | $1.6 \times 10^5$ | $1.6 \times 10^5$ |
| | number of bacteria after 24 hrs (number/ml) | $7.0 \times 10^5$ | $2.1 \times 10^5$ |
| | decreasing rate (%) | | 99.7 |

After manufacturing insole using the manufactured aqueous adhesive and the oil adhesive as adhesive used for manufacturing the insole for shoes, a test on anti-fungal is implemented according to KS K 0693-2001. A result is as shown in Table. 12.

TABLE 12

| sample | testing bacteria | items | blank | sample |
|---|---|---|---|---|
| shoe bottom plate treated with aqueous adhesive | Staphylococcus aureus | initial number of bacteria (#/ml) | $1.2 \times 10^5$ | $1.2 \times 10^5$ |
| | | number of bacteria after 24 hrs (#/ml) | $5.8 \times 10^5$ | <10 |
| | | decreasing rate (%) | | >99.9 |
| | clepsiera neumonia | initial number of bacteria (#/ml) | $1.4 \times 10^5$ | $1.43 \times 10^5$ |
| | | number of bacteria after 24 hrs (#/ml) | $6.4 \times 10^5$ | <10 |
| | | decreasing rate (%) | | >99.9 |
| shoe bottom plate treated with oil adhesive | Staphylococcus aureus | initial number of bacteria (number/ml) | $1.2 \times 10^5$ | $1.2 \times 10^5$ |
| | | number of bacteria after 24 hrs (#/ml) | $5.8 \times 10^5$ | <10 |
| | | decreasing rate (%) | | >99.9 |
| | clepsiera neumonia | initial number of bacteria (number/ml) | $1.4 \times 10^5$ | $1.4 \times 10^5$ |
| | | number of bacteria after 24 hrs (#/ml) | $6.4 \times 10^5$ | <10 |
| | | decreasing rate (%) | | >99.9 |

A Ninth Embodiment

After dipping cotton into the nanocomposite solution, the cotton is added with an anti-fungal and deodoration function by drying at 80° C.

The anti-fungal characteristics are measured according to KS K 0693-2001, and the results are as shown in Table. 13.

TABLE 13

| testing bacteria | items | Blank | Sample |
|---|---|---|---|
| Staphylococcus aureus | the initial # of bacteria (#/ml) | $1.2 \times 10^5$ | $1.2 \times 10^5$ |
| | the # of bacteria after 18 hrs (#/ml) | $5.6 \times 10^5$ | <10 |
| | decreasing rate (%) | | >99.9 |
| clepsiera neumonia | the initial # of bacteria (#/ml) | $1.4 \times 10^5$ | $1.4 \times 10^5$ |
| | the # of bacteria after 18 hrs (#/ml) | $6.3 \times 10^5$ | <10 |
| | decreasing rate (%) | | >99.9 |

The test on deodoration is implemented according to the gas detection method. A variation on a gas concentration is measured according to passage of time on a sample of anti-fungal cotton 3.0 g. Its result is as shown in Table. 14.

TABLE 14

| | | \multicolumn{4}{c}{measured time (min)} | | | |
|---|---|---|---|---|---|
| | | 5 | 15 | 30 | 60 |
| gas | blank | 430 | 370 | 340 | 310 |
| concentration (PPM) | sample | 310 | 260 | 210 | 150 |
| deodoration rate (%) | | 27.9 | 29.7 | 38.2 | 51.6 |

A Tenth Embodiment

A fabric with an anti-fungal function is manufactured by adding the nanocomposite solution according to the embodiment of the present invention. A method of adding is same as the sixth embodiment.

TABLE 15

| testing bacteria | items | Blank | Sample |
|---|---|---|---|
| Staphylococcus aureus | the initial # of bacteria (#/ml) | $1.4 \times 10^5$ | $1.4 \times 10^5$ |
| | the # of bacteria after 18 hrs (#/ml) | $6.4 \times 10^5$ | <10 |
| | decreasing rate (%) | | >99.9 |
| clepsiera neumonia | the initial # of bacteria (#/ml) | $1.5 \times 10^5$ | $1.5 \times 10^5$ |
| | the # of bacteria after 18 hrs (#/ml) | $6.6 \times 10^5$ | <10 |
| | decreasing rate (%) | | >99.9 |

An Eleventh Embodiment

A leather with an anti-fungal function is manufactured by treating the natural leather with the nanocomposite solution. A treatment method is as follows. After refining the leather, ammonia is added to adjust PH to between 8 and 10. The nanocomposite solution is added and acetic acid is used to adjust the PH to between 3 and 5. Herein, the amount of the added nanocomposite solution preferably should be between 1 and 5 weight percentage.

A test on the anti-fungal function of the leather manufactured above is implemented according to (FC-TM-19)-2001. A result is as shown in Table. 16.

TABLE 16

| testing bacteria | items | Blank | Sample |
|---|---|---|---|
| Staphylococcus aureus | initial number of bacteria (number/ml) | $1.3 \times 10^5$ | $1.3 \times 10^5$ |
| | number of bacteria after 24 hrs (number/ml) | $5.7 \times 10^5$ | <10 |
| | decreasing rate (%) | | >99.9 |
| E coli | initial number of bacteria (number/ml) | $1.2 \times 10^5$ | $1.2 \times 10^5$ |
| | number of bacteria after 24 hrs (number/ml) | $5.9 \times 10^6$ | $1.2 \times 10^4$ |
| | decreasing rate (%) | | 99.8 |

A Twelfth Embodiment

A water tissue with the anti-fungal function is manufactured using the nanocomposite solution according to the embodiment of the present invention. The anti-fungal water tissue is manufactured by soaking a dried tissue with the nanocomposite solution. The nanocomposite solution may be diluted for use as well.

A test on the anti-fungal function of the manufactured water tissue is implemented according to a shake-plask method (FC-TM-19)-2001. A result is as shown in Table. 17.

TABLE 17

| testing bacteria | items | Blank | Sample |
|---|---|---|---|
| Staphylococcus aureus | initial number of bacteria (number/ml) | $1.3 \times 10^5$ | $1.3 \times 10^5$ |
| | number of bacteria after 18 hrs (number/ml) | $5.7 \times 10^5$ | <10 |
| | decreasing rate (%) | | >99.9 |
| E coli | initial number of bacteria (number/ml) | $1.2 \times 10^5$ | $1.2 \times 10^5$ |
| | number of bacteria after 18 hrs (number/ml) | $5.9 \times 10^6$ | $1.2 \times 10^4$ |
| | decreasing rate (%) | | 99.8 |

A Thirteenth Embodiment

A coating liquid with the functions of anti-fungal, protecting ultraviolet, and anti insect is manufactured by mixing the nanocomposite solution with the polyurethane emulsion or acrylic emulsion. A mixture ratio is between 0.5 and 2 weight percentages of the nanocomposite solution for 100 weight percentage of the polyurethane or acrylic emulsion.

After manufacturing a sample as film by coating on the glass and drying to measure the anti-fungal function, it was measured according to a film contacting method (FC-TM-21)-2001. The result is as shown in Table. 18.

TABLE 18

| testing bacteria | items | Blank | Sample |
|---|---|---|---|
| Staphylococcus aureus | initial number of bacteria (number/ml) | $1.4 \times 10^5$ | $1.4 \times 10^5$ |
| | number of bacteria after 18 hrs (number/ml) | $5.9 \times 10^5$ | <10 |
| | decreasing rate (%) | | >99.9 |
| E coli | initial number of bacteria (number/ml) | $1.6 \times 10^5$ | $1.6 \times 10^5$ |
| | number of bacteria after 18 hrs (number/ml) | $7.7 \times 10^6$ | <10 |
| | decreasing rate (%) | | >99.9 |

Figure 7:
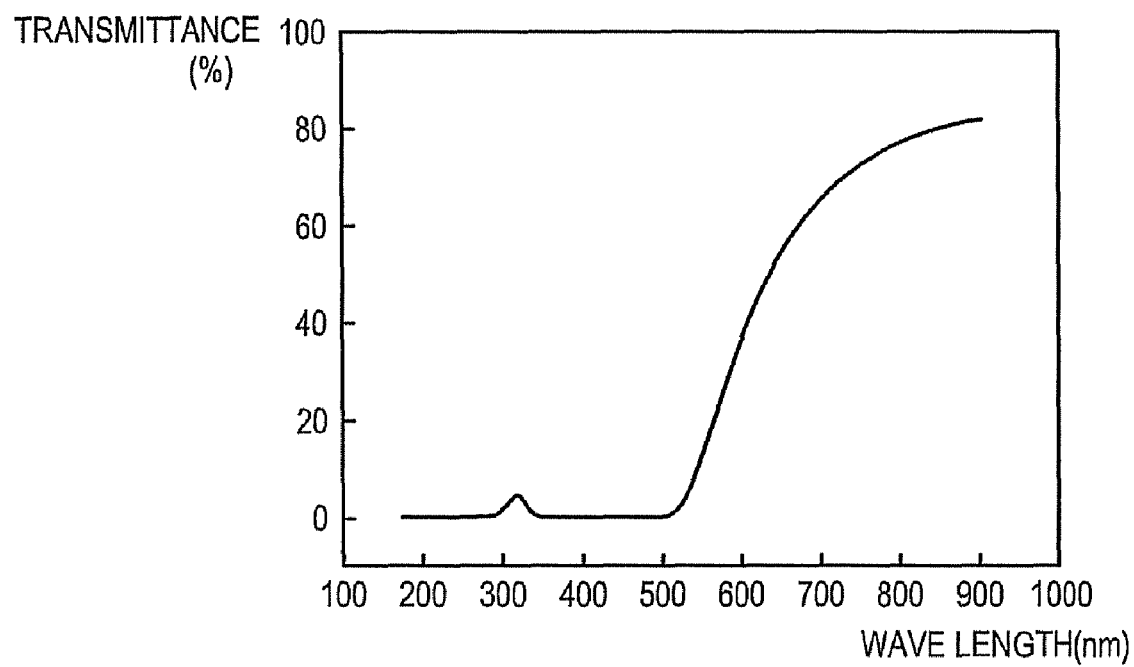
FIG. 7 is a graph representing ultraviolet-visible ray absorption spectrum of polyurethane film dispersed with the nanocomposite.

Also, to observe the ultraviolet protection and radiation effect, a spectrum of ultraviolet-visible ray is measured. A sample is manufactured to be a film with thickness of less than 100 μm by drying the coating liquid, using an ultraviolet-visible ray prism. The result is as shown in FIG. 7. It is noted that the film absorbs the ultraviolet of up to 500 nm.

A Fourteenth Embodiment

A conductive coating liquid is manufactured by adding gelatin binder to the nanocomposite solution according to the embodiment of the present invention. Herein, the amount of the added gelatin is adjusted to be 0.5 weight percentage relative to the nanocomposite solution. After coating the liquid on glass, it was treated with heat at various temperatures. A variation of the conductivity according to the temperature of heat process is shown in Table. 19.

TABLE 19

| | heat process temperature | | |
|---|---|---|---|
| | normal temperature | 200° C. | 400° C. |
| surface resistance | $10^9 \, \Omega$ | $10^4 \, \Omega$ | $2.5 \, \Omega$ |

A Fifteenth Embodiment

Inorganic coating agent with anti-fungal function is manufactured by adding $NaSiO_3$ to the nanocomposite solution according to the embodiment of the present invention. This coating agent is manufactured by adding $NaSiO_3$ of weight percentage between 5 and 20. It has a characteristic that the coating can be done without additional heat process on the glass.

A Sixteenth Embodiment

A plastic composite with anti-fungal function is manufactured by mixing the nanocomposite solution to a mixture/casting process of the plastic material.

The dispersion media of the nanocomposite solution is preferably removed in the mixture/casting process.

The amount of the nanocomposite solution may be between 0.01 and 10 weight percentage for 100 weight percentage of the plastic material.

In a case that the dispersion media is water, at least one of the dispersion media selected out of a group comprising the zinc stearate, amaid wax, polyesthylen wax, polyprophylene wax, calcium stearate may be added. The content is preferably between 0.01 and 0.5 weight percentage for 100 weight percentage of the plastic.

The plastic material may employ polyprophelene, atrylonytrylstyrene, polycarbonate, polyesterecelphone, nylon, polyethylene, and polybuthylsteren. However, it is not limited to those.

The mixture/casting process may comprise a process to manufacture a master alignment including the nanocomposite solution.

Hereinbelow, examples applied with the nanocomposite solution are described.

100 weight percentage of polyprophylene resin (J-320 from HONAM refinery co.) and 0.5 weight percentage of zinc stearate (Hi-flow from SHINWON chemical co.) and 0.5 weight percentage of the polyethylene wax (L-C 121N from lion comtec co.) are mixed in a mixer. After mixing for 5 minutes with the number of rotation of 500, 5 weight percentage of the nanocomposite solution is put into the mixture and mixed for 60 minute with 600 of rotations. After mixing, a temperature is kept at 200° C. C. The mixed polyprophylene resin is put in a mixer to manufacture polyprophylene master batch containing 0.5 weight percentage of the nanocomposite solution. In this way, 90 weight percentage of the polyprophylene (J-320 from HONAM refinery co.) not containing the nanocomposite solution and 10 weight percentage of polyprophylene master batch are mixed before casting. Herein, the temperature of the mixer is 200° C.

A test of the anti-fungal and far infrared radiation is implemented on a sample from the polyprophylene outputs. The sample manufactured as described above is tested with the anti-fungal test according to the film contacting method (FC-TM-21)-2001. The result is as shown in Table. 20.

TABLE 20

| testing bacteria | items | Blank | Sample |
|---|---|---|---|
| Staphylococcus aureus | initial number of bacteria (number/ml) | $1.4 \times 10^5$ | $1.4 \times 10^5$ |
| | number of bacteria after 18 hrs (number/ml) | $6.4 \times 10^6$ | $1.9 \times 10^4$ |
| | decreasing rate (%) | | 99.7 |
| E coli | initial number of bacteria (number/ml) | $1.6 \times 10^5$ | $1.6 \times 10^5$ |
| | number of bacteria after 18 hrs (number/ml) | $6.9 \times 10^6$ | <10 |
| | decreasing rate (%) | | >99.9 |

A far infrared radiation test is implemented on the sample manufactured as described above. The result is as shown in Table. 21.

TABLE 21

| radiation rate (5~20 μm) | radiation energy (W/m$^2$) |
|---|---|
| 0.893 | $3.60 \times 10^2$ |

As described above, the nanocomposite solution with multi-functions and the preparation method thereof according to the embodiment of the present invention employs an environment-friendly electrolysis method. Accordingly, it does not discharge pollutant and is highly productive, applicable to industry.

Also, as the present invention provides a method to strongly and electrically bind the silica nano particle and silver nano particle, which are inorganic particles. It can contribute to advancement of technology on binding the inorganic particle and the metal particle of nano sizes in the future.

The nanocomposite and the nanocomposite solution manufactured according to the embodiment of the present invention can solve a problem of safe custody caused by ionization characteristic of conventional silver colloidal and the silver nano solution. Also, it can be mixed with the chlorine or solution with reactive anion, and it shows an excellent thermal stability up to 100° C.

Although a few embodiments of the present invention have been shown and described, it will be appreciated by those skilled in the art that changes may be made in these embodiments without departing from the principles and spirit of the invention, the scope of which is defined in the appended claims and their equivalents.

What is claimed is:

1. A method for preparation of nanocomposite solution, comprising:
   preparing basic silica colloid aqueous solution;
   providing an electrolysis apparatus by installing a negative electrode containing aluminum and a positive electrode containing silver into the basic silica colloid aqueous solution; and
   forming nanocomposite by applying voltage to the respective electrodes of the electrolysis apparatus.

2. The method for preparation of the nanocomposite solution according to claim 1, wherein temperature when applying the voltage is between 30 and 100° C.

3. The method for preparation of the nanocomposite solution according to claim 1, wherein content of silica in the basic silica colloid aqueous solution is between 0.1 and 30 weight percentage.

4. The method for preparation of the nanocomposite solution according to claim 1, wherein PH of the basic silica colloid aqueous solution is between 8 and 12 PH.

5. The method for preparation of the nanocomposite solution according to claim 1, further comprising applying organic solvent to the nanocomposite solution and removing water.

* * * * *